United States Patent [19]

Lilly, Jr. et al.

[11] 4,166,973
[45] Sep. 4, 1979

[54] METHOD AND SYSTEM FOR DETECTION OF THIN METAL LAYERS IN PACKAGED ARTICLES

[75] Inventors: A. Clifton Lilly, Jr.; Francis M. Watson, III; Peter Martin; John S. Price, all of Richmond, Va.

[73] Assignee: Philip Morris Incorporated, New York, N.Y.

[21] Appl. No.: 884,367

[22] Filed: Mar. 7, 1978

[51] Int. Cl.² .................................................. G01R 27/04
[52] U.S. Cl. ............................... 324/58.5 B; 209/571
[58] Field of Search ..................... 324/58.5 B, 58 B; 209/571, 576, 587

[56] References Cited

U.S. PATENT DOCUMENTS

| | | | |
|---|---|---|---|
| 2,609,422 | 9/1952 | Hulstede | 324/58 B |
| 3,263,166 | 7/1966 | Augustine et al. | 324/58.5 B |
| 3,401,333 | 9/1968 | Thompson | 324/58.5 B |
| 3,451,546 | 6/1969 | Murley, Jr. | 209/576 |
| 3,473,111 | 10/1969 | Leersnijder et al. | 209/571 X |
| 3,710,243 | 1/1973 | Keenan | 324/58.5 B |
| 3,942,107 | 3/1976 | Gerhard | 324/58 B X |
| 4,045,727 | 8/1977 | Yu et al. | 324/58.5 B |

OTHER PUBLICATIONS

Summerhill, Microwaves as an Industrial Tool, Measurement & Instrument Review, Feb. 1969, pp. 79-81.
Pa Proximity Logic Modules, Metal Detectors-Proximity Controls, pp. 40 & 41.
Poole, Jr., Electron Spin Resonance, Interscience Publishers, 1967, pp. 237-240.

Primary Examiner—Stanley T. Krawczewicz
Attorney, Agent, or Firm—Watson, Leavenworth, Kelton & Taggart

[57] ABSTRACT

Metal layers of extreme thinness, of the order of fifty Angstroms and greater are detected by use of microwave energy so propagated as to permit determination of the presence or absence of the metal in a detection zone of limited extent outwardly of the issuance location of such propagated energy. Apparatus is provided for propagating microwave energy having a characteristic which changes with propagation distance from a maximum value at the energy issuance location to a minimum value first exhibited at the outward end of the detection zone.

15 Claims, 5 Drawing Figures

4,166,973

METHOD AND SYSTEM FOR DETECTION OF THIN METAL LAYERS IN PACKAGED ARTICLES

FIELD OF THE INVENTION

This invention relates generally to methods and systems for examining packaging integrity and pertains more particularly to detecting the presence or absence of package underlayers comprised of metallized sheet material.

BACKGROUND OF THE INVENTION

It has long been customary in containers, such as cigarette packages, to include metal foil material for interior encasement of articles. This material itself has given rise to systems for quality control of packaging, functioning for cigarette packaging to assess whether the parent container for cartons has its required number of individual cartons, whether each carton has its full complement of individual packs and whether each individual pack has its metal foil interior layer.

There has recently been developed a substitute for the conventional metal foil for packaging use, differing primarily from the metal foil in thickness, the substitute being comprised of a carrier or substrate, such as paper, on which is deposited an extremely thin layer of metal, such as aluminum, having thickness approximately one seven hundredth of that of the metal foil. While the customary sheet material has long been detected by radio-frequency field-generating detectors, the substitute material has avoided sensing by such conventional r-f detectors by reason of its reduced thickness. Absent viable detection method and system for the newer packaging material, its benefits of lessened weight and reduced cost remain unavailable to the packaging industry.

SUMMARY OF THE INVENTION

It is the object of the present invention to provide method and systems for detection of the presence or absence of metal layers of extreme thinness within packages.

In attaining the foregoing and other objects, the present invention provides methods and systems employing microwave energy for such detection practice. As is developed below, the invention tolerates a practical measure of relative displacement of detector/transmitter apparatus and an object being examined, by so propagating microwave energy as to define a non-ambiguous measurement zone having linewise extent exceeding such practical displacement measure. Further, the pattern of energy propagation is such as to permit ready discrimination as between energy reflections originating within and without the detection zone. The methods and systems of the invention are accordingly suited for use in industrial environments, for example, in examining packages having articles, which may be in stacks, in the course of active conveyance of packages in microwave energy-reflective backgrounds. In further explanation of the background of the invention, attention is invited to the prior art statement filed herein pursuant to 37 CFR 1.97 and 1.98.

The foregoing and other objects and features of the invention will be further understood from the following detailed description of preferred embodiments and practices thereof and from the drawings wherein like reference numerals identify like parts throughout.

DESCRIPTION OF PREFERRED EMBODIMENTS AND PRACTICES

Figure 1:
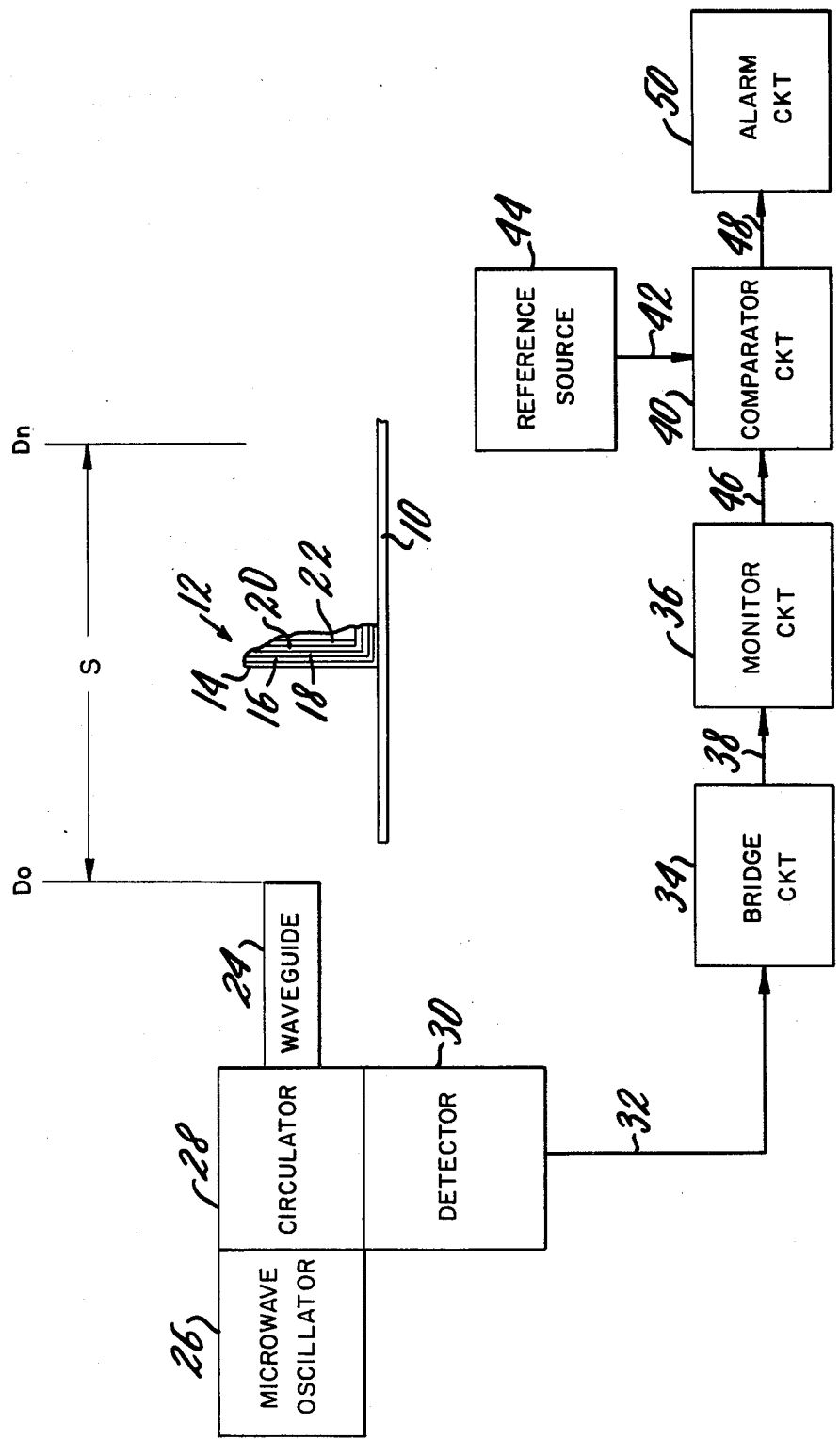
FIG. 1 is a schematic block diagram of the preferred system of the invention, shown together with a conveyed article being examined.

Referring to FIG. 1, conveyor 10 supports articles for movement outwardly of the plane of FIG. 1, article 12 being shown as a cigarette carton having cardboard outer layer 14, the usual cigarette pack plastic film 16, the pack identifying paper wrap 18, the above-discussed thin metallized paper 20 and lastly cigarettes 22. In the course of carton movement, each of its contained packs passes waveguide 24, whereby the presence or absence of the metallized paper is detected.

Microwave oscillator 26 generates energy in the microwave frequency regions suitable for reflectance by metal of thicknesses, for example, seventy-five Angstroms, present in the metallized paper. Oscillator 26 may be a Gunn oscillator, Plessey Semiconductor GDVO-3/001, operated on connection to an eight volt direct-current power supply to provide oscillations of about ten and one-half gigacycles ($10.5 \times 10^9$ hertz). Circulator 28 has one port thereof connected to oscillator 26 and may be any three-port circulator, such as a Wavetek S-4517 circulator. A second port of circulator 28 is connected to waveguide 24 and the third circulator port is connected to detector 30.

Change in the output signal of detector 30, occasioned by energy returned to waveguide 24 on metal detection, is conducted by line 32 to self-balancing bridge circuit 34 whose output signal is conducted to monitor circuit 36 over line 38. Units 30, 34 and 36 and lines 32 and 38 may be constituted either by a Schottky Barrier diode detector or other power monitor, such as Hewlett-Packard Power Monitor Model No. 432A.

Comparator circuit 40 has a first input from line 42, which is a reference voltage provided by reference source 44, and a second input from monitor circuit 36 over line 46. When the second input is less than the first input, indicative of the detection of the absence of the metallized paper, circuit 40 applies a signal to its output line 48 of character energizing alarm circuit 50.

In addressing the particular industrial situation of cigarette packaging, applicants predetermined an outside limit to the possible spacing of the metallized paper with respect to the point of issuance of radiant energy. Such spacing is indicated by the reference letter S in FIG. 1 and is the spacing between issue location $D_o$ (the end of waveguide 24) and a maximum rightward position $D_n$ of the article on the conveyor. By way of example, such spacing was determined to be approximately three-quarters of an inch, i.e., about nineteen millimeters.

Figure 2:
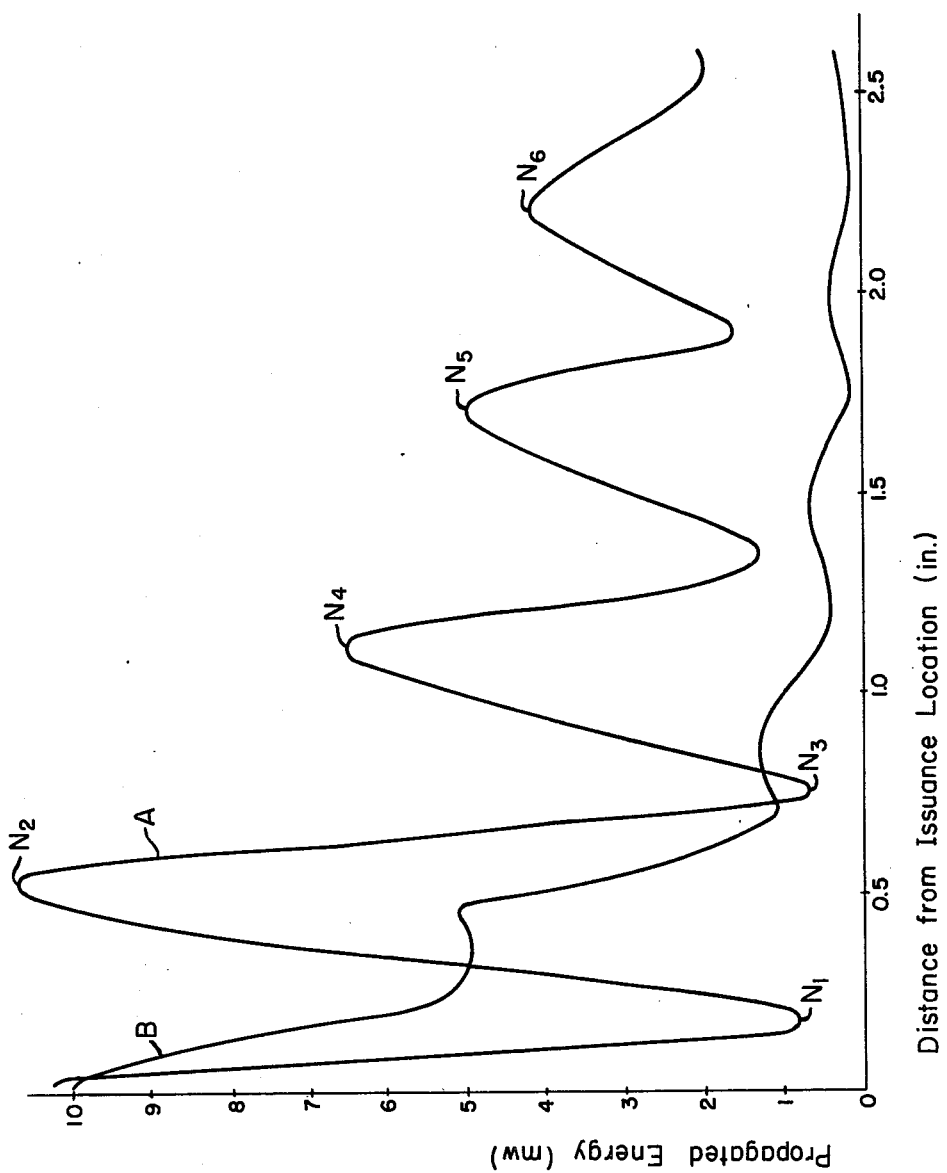
FIG. 2 shows in curve A microwave energy propagation with distance for standing waves in conventional waveguide usage and shows in curve B microwave energy propagation with distance in modified practice in accordance with the invention.

In use of the customary rectangular waveguide as waveguide 24, the usual propagation pattern of curve A of FIG. 2 was observed, with plural nodes $N_1$, $N_2$ and $N_3$ occurring between $D_o$ through $D_n$. Resulting ambiguity in detection of the actual presence of the metallized paper was traced to the ambiguities inherent in the propagation pattern. Thus, an article so situated on the conveyor that the metal layer is in nodal positions $N_1$ and $N_3$ will be identified as an article without metallized paper or as a missing article, despite its presence with metallized paper. Additional ambiguity arises from "far field" reflection, where the examined article is missing or present without metallized paper. Thus, a reflective surface disposed outside of the detection zone defined by spacing S, for example, at or about any of nodal positions $N_4$ through $N_6$, will reflect energy of like magnitude to that reflected by metallized paper disposed about midway between $N_1$-$N_3$. Indeed, such curve A carries onto great distance beyond node $N_6$ centered about a power level of about 2.75 mw. Since detector 30 cannot distinguish between such reflected energies as to origin, conveyor structure or other reflective apparatus therebeyond can give rise to suppression of a packaging error.

In providing method and practice enabling non-ambiguous detection with microwave energy, the invention provides for propagating microwave energy into the preselected residence zone for the metallized paper such that an energy return will be observable for metal located at all positions throughout the zone and such that energy return from metal beyond such zone will have a characteristic, lessened amplitude, enabling ready distinction thereof. A suitable transmitted energy propagation characteristic for this purpose is shown in curve B of FIG. 2 and will be seen to have decreasing amplitude with distance outwardly of issue location $D_o$ to location $D_n$. Whereas the standing wave pattern of curve A of FIG. 2 exhibits cyclic sinusoidal amplitude variation, the pattern of curve B exhibits its maximum amplitude characteristic at the waveguide issuance location and its minimum amplitude characteristic only as one exits the detection zone, i.e., at about 0.7 in. beyond the issuance location at the outward end of the distance range through the detection zone. The distance over which the maximum to minimum value change occurs is of measure exceeding the standing wave wavelength at the operative frequency. There is thus no reversion from a minimum characteristic value to values greater than minimum value throughout the detection zone and hence no locations exist within the detection zone where metallized paper may be located and not reflect energy above a threshold value below such minimum amplitude characteristic. Beyond the detection zone exit, curve B exhibits sinusoidal change in the customary standing wave manner, but at no point has an amplitude characteristic which exceeds such threshold. Hence, energy reflected from reflective structure at locations corresponding to nodal positions $N_4$-$N_6$ of curve A may be distinguished and rejected on the basis of amplitude.

Figure 3:
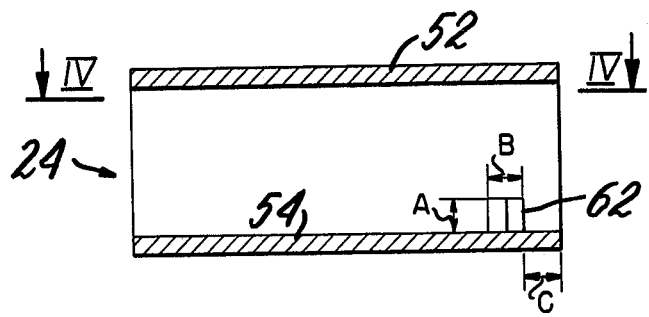
FIG. 3 is a front sectional elevation of a waveguide for use in practicing the invention the section being as seen from plane II—II of FIG. 4.
Figure 4:
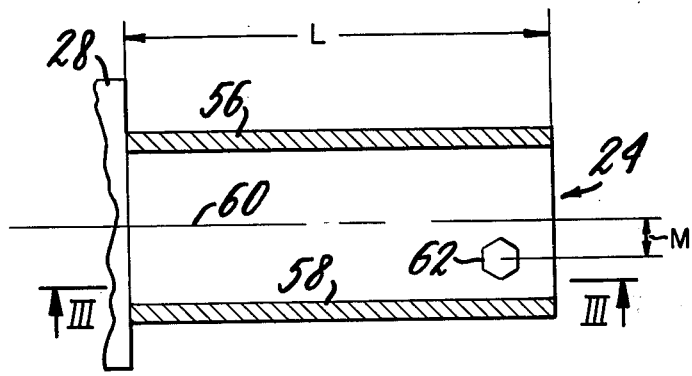
FIG. 4 is a plan sectional view of the FIG. 3 waveguide as seen from plane IV—IV of FIG. 3.
Figure 5:
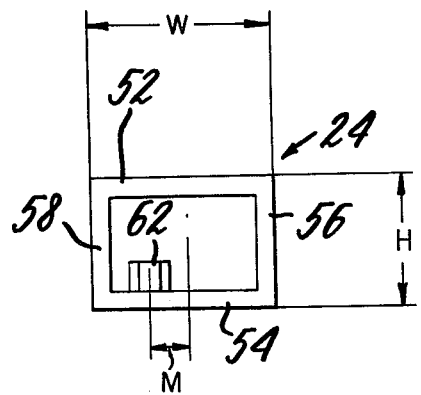
FIG. 5 is a side elevation of the FIG. 3 waveguide.

Referring to FIGS. 3-5, the conventional rectangular waveguide is shown modified as waveguide 24 having top wall 52 and bottom wall 54, and sidewalls 56 and 58 extending parallel with waveguide central/longitudinal axis 60. Electrically conductive member 62, which may be constituted by a hexagonal metal nut or the like is disposed fixedly on bottom wall 54 at a spacing aside axis 60 of measure M. In an embodiment implemented and found to yield the propagation pattern of curve B of FIG. 2, dimension L of FIG. 4 was 46 mm., dimension W of FIG. 5 was 25.4 mm., dimension H of FIG. 5 was 12.7 mm., dimensions A, B and C of FIG. 3 were 2, 7 and 5 mm., respectively, and measure M was 3 mm. The waveguide wall thickness was 1.25 mm. Curve B of FIG. 2 defines the amplitude characteristic as it exists coincident with axis 60 of FIG. 4 and rightwardly of the issuance end of waveguide 24. Like amplitude characteristics, i.e., extending from maximum to minimum values without reversion to minimum value throughout the detection zone, are observed linewise rightwardly of the waveguide issuance end in mutually orthogonal planes, e.g., horizontal and vertical, containing axis 60.

As is known to those skilled in the microwave arts, the size of transmitting and receiving apparatus increases greatly as one seeks to operate in lower frequency portions of the microwave frequency range. Thus, in the portion of the microwave frequency range noted as exemplary above for the subject invention, about ten gigacycles, one enjoys a minimization of component size and attendant cost savings. While such size and cost advantage would be accompanied by attendant increase in the number of nodes in the detection zone in customary traveling wave propagation and correspondingly higher possible ambiguity, such ambiguity is eliminated by applicant's correlation of propagation pattern and residence range of the matter to be detected. While the invention contemplates its use at lower radiant energy frequencies, it renders unnecessary the choice of lower frequency simply for lessening ambiguity. Preferably, the invention is practiced with the highest frequency apparatus commercially practical.

Various changes may evidently be introduced in the foregoing practices and embodiments without departing from the invention. Other propagation patterns which serve equally well to eliminate standing wave ambiguity as respects both detection zone positioning of objects and spurious reflections from outside such zone, as well as apparatus for generating such propagation patterns will be evident to those skilled in the art. Likewise, the above-noted apparatus for implementing the invention, which is commonly available commercially in parts as indicated, is subject to great variation as will be appreciated by skilled artisans. Accordingly, the particularly disclosed practices and embodiments are intended in an illustrative and not in a limiting sense. The true spirit and scope of the invention is set forth in the following claims.

What is claimed is:

1. In a method for detecting the presence or absence of radiant energy-reflective matter in an article, the steps of:
   (a) generating radiant energy at a predetermined frequency;
   (b) defining a location for issuance of such generated radiant energy and preselecting a distance range outwardly of such issuance location within which said article may be positioned during such detection; and
   (c) propagating said generated radiant energy outwardly of said issuance location in pattern having a maximum characteristic value at said issuance location and a minimum value in said distance range first exhibited at the outward end of said distance range.

2. The method claimed in claim 1 wherein said step (c) is practiced further by propagating said generated radiant energy in pattern having characteristic values throughout distances beyond said outward end of said distance range which are less than said characteristic minimum value in said distance range.

3. The method claimed in claim 1 wherein said propagation characteristic is the voltage amplitude of said propagated radiant energy.

4. The method claimed in claim 3 wherein said propagated radiant energy is microwave energy.

5. The method claimed in claim 2 wherein said propagation characteristic is the voltage amplitude of said propagated radiant energy.

6. The method claimed in claim 5 wherein said propagated radiant energy is microwave energy.

7. A method for use in detecting the presence or absence of a thin metal layer in a packaged article, comprising the steps of:
   (a) generating microwave energy at a preselected frequency;
   (b) defining a location for issuance of such generated microwave energy and preselecting a distance range outwardly of said issuance location within which said layer may be positioned during such detection; and
   (c) propagating said generated microwave energy outwardly of said issuance location in pattern having a maximum characteristic value at said issuance location and a minimum value in said distance range first exhibited at the outwardmost extent of said distance range.

8. The method claimed in claim 7 wherein said step (c) is practiced further by propagating said generated microwave energy in pattern having characteristic values throughout distances beyond said outward end of said distance range which are less than said characteristic minimum value in said distance range.

9. The method claimed in claim 7 wherein said propagation characteristic is the voltage amplitude of said propagated radiant energy.

10. The method claimed in claim 8 wherein said propagation characteristic is the voltage amplitude of said propagated radiant energy.

11. The method claimed in claim 7 wherein said article is conveyed and wherein said step (b) is practiced by preselecting a distance range encompassing different positioning of said layer transversely of the direction of conveyance thereof.

12. The method claimed in claim 8 wherein said article is conveyed and wherein said step (b) is practiced by preselecting a distance range encompassing different positioning of said layer transversely of the direction of conveyance thereof.

13. A system for use in detecting the presence or absence of a thin metal layer in a packaged article, comprising:
   (a) means for generating microwave energy at a preselected frequency;
   (b) means for propagating such generated microwave energy outwardly of an issuance location therefor in pattern having a maximum characteristic value at said issuance location and a minimum value first exhibited with distance at a distance spaced outwardly of said issuance location by a measure exceeding the standing wave wavelength at said preselected frequency; and
   (c) detector means for receiving energy reflected to said issuance location and for generating an output signal when such received energy exhibits a characteristic of value less than a preselected threshold characteristic value.

14. The system claimed in claim 13 wherein said means (b) comprises a waveguide and means disposed in said waveguide for affecting such propagation of said generated energy.

15. The system claimed in claim 14 wherein said means disposed in said waveguide comprises an electrically conductive member disposed in spaced relation to the central longitudinal axis of said waveguide.

* * * * *